(12) United States Patent
Meyer et al.

(10) Patent No.: US 7,540,881 B2
(45) Date of Patent: Jun. 2, 2009

(54) BIFURCATION STENT PATTERN

(75) Inventors: Michael P. Meyer, Richfield, MN (US);
Daniel Gregorich, St. Louis Park, MN (US); Shawn Sorenson, Maple Grove, MN (US); Richard C. Tooley, Crystal, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 11/315,084

(22) Filed: Dec. 22, 2005

(65) Prior Publication Data
US 2007/0150046 A1     Jun. 28, 2007

(51) Int. Cl.
*A61F 2/06* (2006.01)
(52) U.S. Cl. .................. 623/1.35; 623/1.15; 623/1.22
(58) Field of Classification Search ............... 623/1.15, 623/1.36, 1.16, 1.35; A61F 2/06
See application file for complete search history.

(56) References Cited

U.S. PATENT DOCUMENTS

| | | | | |
|---|---|---|---|---|
| 6,013,091 A | 7/1980 | Dahms | ................ | 83/150 |
| 4,309,994 A | 1/1982 | Grunwald | ............... | 128/214 R |
| 4,769,005 A | 9/1988 | Ginsburg et al. | ............. | 604/53 |
| 4,774,949 A | 10/1988 | Fogarty | .................. | 128/348.1 |
| 4,896,670 A | 1/1990 | Crittenden | ................ | 606/194 |
| 4,905,667 A | 3/1990 | Foerster et al. | ................ | 128/4 |
| 4,994,071 A | 2/1991 | MacGregor | ................ | 606/194 |
| 5,325,826 A | 7/1994 | Vardi et al. | ............... | 623/1.35 |
| 5,342,387 A | 8/1994 | Summers | .................... | 606/198 |
| 5,387,235 A | 2/1995 | Chuter | ........................ | 623/1 |
| 5,456,712 A | 10/1995 | Maginot | ....................... | 623/1 |
| 5,476,471 A | 12/1995 | Shifrin et al. | ............... | 606/151 |
| 5,487,730 A | 1/1996 | Marcadis et al. | ............. | 604/96 |
| 5,591,228 A | 1/1997 | Edoga | ........................ | 623/1 |
| 5,596,020 A | 1/1997 | Morris | ....................... | 516/646 |
| 5,607,444 A | 3/1997 | Lam | ............................ | 606/194 |
| 5,609,605 A | 3/1997 | Marshall et al. | ............. | 606/191 |
| 5,609,627 A | 3/1997 | Goicoechea et al. | ........... | 623/1 |
| 5,613,980 A | 3/1997 | Chauhan | ..................... | 606/194 |
| 5,617,878 A | 4/1997 | Taheri | ........................ | 128/898 |
| 5,632,762 A | 5/1997 | Myler | ......................... | 606/194 |

(Continued)

FOREIGN PATENT DOCUMENTS

CA        2220864        7/1999

(Continued)

OTHER PUBLICATIONS

U.S. Appl. No. 09/325,996, filed Jun. 4, 1999, Vardi et al.

(Continued)

*Primary Examiner*—Corrine M McDermott
*Assistant Examiner*—Jason-Dennis Stewart
(74) *Attorney, Agent, or Firm*—Vidas, Arrett & Steinkraus, P.A.

(57) ABSTRACT

A stent may comprise a plurality of serpentine bands connected by connector struts. The stent may further comprise a side branch cell having a plurality of outwardly deployable petals. Each serpentine band may have an approximate longitudinal axis. A portion of the serpentine bands may be flared in the unexpanded state, wherein a portion of the axis of each flared band is oriented helically about a portion of the stent. The bands may reorient during stent expansion, whereafter the axis of each band is oriented in a circumferential direction.

21 Claims, 4 Drawing Sheets

U.S. PATENT DOCUMENTS

| | | | |
|---|---|---|---|
| 5,632,763 A | 5/1997 | Glastra | 606/194 |
| 5,632,772 A | 5/1997 | Alcime et al. | 623/1 |
| 5,636,641 A | 6/1997 | Fariabi | 600/585 |
| 5,669,924 A | 9/1997 | Shaknovich | 606/108 |
| 5,669,932 A | 9/1997 | Fischell et al. | 606/198 |
| 5,676,697 A | 10/1997 | McDonald | 623/1 |
| 5,683,450 A | 11/1997 | Goicoechea et al. | 623/1 |
| 5,697,971 A | 12/1997 | Fischell et al. | 623/1 |
| 5,707,348 A | 1/1998 | Krogh | 602/41 |
| 5,709,713 A | 1/1998 | Evans et al. | 623/1 |
| 5,720,735 A | 2/1998 | Dorros | 604/284 |
| 5,749,825 A | 5/1998 | Fischell et al. | 600/3 |
| 5,749,890 A | 5/1998 | Shaknovich | 606/198 |
| 5,755,734 A | 5/1998 | Richter et al. | 606/194 |
| 5,755,735 A | 5/1998 | Richter et al. | 606/194 |
| 5,755,771 A | 5/1998 | Penn et al. | 623/1 |
| 5,755,773 A | 5/1998 | Evans et al. | 623/1 |
| 5,755,778 A | 5/1998 | Kleshinski | 623/1 |
| 5,782,906 A | 7/1998 | Marshall et al. | 623/1 |
| 5,824,036 A | 10/1998 | Lauterjung | 623/1 |
| 5,824,040 A | 10/1998 | Cox et al. | 623/1 |
| 5,827,320 A | 10/1998 | Richter et al. | 606/194 |
| 5,851,464 A | 12/1998 | Davila et al. | 264/103 |
| 5,868,777 A | 2/1999 | Lam | 606/194 |
| 5,893,887 A | 4/1999 | Jayaraman | 623/1 |
| 5,906,640 A | 5/1999 | Penn et al. | 623/1 |
| 5,922,021 A | 7/1999 | Jang | 623/1 |
| 5,961,548 A | 10/1999 | Shmulewitz | 623/1 |
| 5,972,017 A | 10/1999 | Berg et al. | 606/198 |
| 6,013,054 A | 1/2000 | Jiun Yan | 604/96 |
| 6,017,324 A | 1/2000 | Tu et al. | 604/96 |
| 6,017,363 A | 1/2000 | Hojeibane | 623/1 |
| 6,030,414 A | 2/2000 | Taheri | 623/1 |
| 6,033,433 A | 3/2000 | Ehr et al. | 623/1 |
| 6,033,434 A | 3/2000 | Borghi | 623/1 |
| 6,033,435 A | 3/2000 | Penn et al. | 623/1 |
| 6,048,361 A | 4/2000 | Von Oepen | 623/1 |
| 6,056,775 A | 5/2000 | Borghi et al. | |
| 6,059,824 A | 5/2000 | Taheri | 623/1 |
| 6,068,655 A | 5/2000 | Seguin et al. | 623/1 |
| 6,086,611 A | 7/2000 | Duffy et al. | 623/1 |
| 6,093,203 A | 7/2000 | Uflacker | 612/1.12 |
| 6,096,073 A | 8/2000 | Webster et al. | 623/1.16 |
| 6,099,497 A | 8/2000 | Adams et al. | 604/96.01 |
| 6,113,579 A | 9/2000 | Eidenschink et al. | 604/264 |
| 6,117,117 A | 9/2000 | Mauch | 604/284 |
| 6,117,156 A | 9/2000 | Richter et al. | 606/194 |
| 6,123,721 A | 9/2000 | Jang | 623/1.6 |
| 6,129,738 A | 10/2000 | Lashinski et al. | 606/194 |
| 6,129,754 A | 10/2000 | Kanesaka | 623/1 |
| 6,142,973 A | 11/2000 | Carleton et al. | 604/96 |
| 6,143,002 A | 11/2000 | Vietmeier | 606/108 |
| 6,159,238 A | 12/2000 | Killion et al. | 612/1.11 |
| 6,165,195 A | 12/2000 | Wilson et al. | 606/194 |
| 6,168,621 B1 | 1/2001 | Vrba | 623/1.2 |
| 6,183,509 B1 | 2/2001 | Dibie | 623/1.35 |
| 6,203,568 B1 | 3/2001 | Lombardi et al. | 623/1.13 |
| 6,210,380 B1 | 4/2001 | Mauch | 604/284 |
| 6,210,429 B1 | 4/2001 | Vardi et al. | 623/1.11 |
| 6,210,433 B1 | 4/2001 | Larre | 623/1.15 |
| 6,231,598 B1 * | 5/2001 | Berry et al. | 623/1.15 |
| 6,254,593 B1 | 7/2001 | Wilson | 606/1.11 |
| 6,258,115 B1 | 7/2001 | Dubrul | 606/200 |
| 6,258,116 B1 | 7/2001 | Hojeibane | 623/1.16 |
| 6,261,305 B1 | 7/2001 | Marotta et al. | 606/200 |
| 6,261,316 B1 | 7/2001 | Shaolian et al. | 623/1.11 |
| 6,264,662 B1 | 7/2001 | Lauterjung | 606/108 |
| 6,264,686 B1 | 7/2001 | Rieu et al. | 623/1.16 |
| 6,290,673 B1 | 9/2001 | Shanley | 604/102.02 |
| 6,293,968 B1 | 9/2001 | Taheri | 623/1.15 |
| 6,325,822 B1 | 12/2001 | Vardi et al. | 623/1.35 |
| 6,325,826 B1 | 12/2001 | Vardi | 623/1 |
| 6,334,864 B1 | 1/2002 | Amplatz et al. | 606/200 |
| 6,334,870 B1 | 1/2002 | Ehr | 623/1.5 |
| 6,346,089 B1 | 2/2002 | Dibie | 603/1.15 |
| 6,348,065 B1 | 2/2002 | Brown | 623/1 |
| 6,355,060 B1 | 3/2002 | Lenker et al. | 623/1.34 |
| 6,358,552 B1 | 3/2002 | Mandralis et al. | |
| 6,361,544 B1 | 3/2002 | Wilson et al. | 606/194 |
| 6,361,555 B1 | 3/2002 | Wilson | 623/1.11 |
| 6,383,213 B2 | 5/2002 | Wilson et al. | 623/1.11 |
| 6,395,018 B1 | 5/2002 | Castaneda | 623/1.13 |
| 6,423,091 B1 | 7/2002 | Hojeibane | |
| 6,436,104 B2 | 8/2002 | Hojeibane | 606/108 |
| 6,436,134 B2 | 8/2002 | Richter | 623/1.15 |
| 6,478,816 B1 | 11/2002 | Kveen et al. | 623/1.15 |
| 6,508,836 B2 | 1/2003 | Wilson et al. | 623/1.35 |
| 6,517,558 B2 | 2/2003 | Gittings et al. | 606/153 |
| 6,520,988 B1 | 2/2003 | Colombo et al. | 623/1.35 |
| 6,540,779 B2 | 4/2003 | Richter et al. | 623/1.35 |
| 6,551,351 B2 | 4/2003 | Smith et al. | |
| 6,579,309 B1 | 6/2003 | Loos | 623/1.16 |
| 6,579,312 B2 | 6/2003 | Wilson et al. | 623/1.35 |
| 6,582,394 B1 | 6/2003 | Reiss | 604/96 |
| 6,596,020 B2 | 7/2003 | Vardi et al. | 623/1.11 |
| 6,599,315 B2 | 7/2003 | Wilson | 623/1.11 |
| 6,599,316 B2 | 7/2003 | Vardi et al. | 623/1.15 |
| 6,645,242 B1 | 11/2003 | Quinn | 623/1.16 |
| 6,689,156 B1 | 2/2004 | Davidson et al. | 623/1.11 |
| 6,692,483 B2 | 2/2004 | Vardi et al. | 604/529 |
| 6,695,877 B2 | 2/2004 | Brucker et al. | 623/1.16 |
| 6,706,062 B2 | 3/2004 | Vardi et al. | 623/1.15 |
| 6,749,628 B1 | 6/2004 | Callol et al. | 623/1.15 |
| 6,776,793 B2 | 8/2004 | Brown et al. | 623/1.15 |
| 6,811,566 B1 | 11/2004 | Penn et al. | 623/1.15 |
| 6,835,203 B1 | 12/2004 | Vardi et al. | 623/1.34 |
| 6,858,038 B2 | 2/2005 | Heuser | 623/1.35 |
| 6,884,258 B2 | 4/2005 | Vardi et al. | 623/1.11 |
| 6,896,699 B2 | 5/2005 | Wilson et al. | 623/1.35 |
| 6,932,837 B2 | 8/2005 | Amplatz et al. | 623/1.15 |
| 6,955,687 B2 | 10/2005 | Richter et al. | 623/1.35 |
| 6,955,688 B2 | 10/2005 | Wilson et al. | 623/1.35 |
| 6,962,602 B2 | 11/2005 | Vardi et al. | 623/1.11 |
| 7,018,400 B2 | 3/2006 | Lashinski et al. | 623/1.11 |
| 7,056,323 B2 | 6/2006 | Mareiro et al. | 606/108 |
| 7,060,091 B2 | 6/2006 | Killion et al. | 623/1.15 |
| 7,169,175 B2 | 1/2007 | Cottone, Jr. et al. | |
| 2001/0003161 A1 | 6/2001 | Vardi et al. | 623/1.11 |
| 2001/0004706 A1 | 6/2001 | Hojeibane | 623/1.11 |
| 2001/0004707 A1 | 6/2001 | Dereume et al. | 623/1.16 |
| 2001/0012927 A1 | 8/2001 | Mauch | 604/284 |
| 2001/0016766 A1 | 8/2001 | Vardi et al. | 623/1.11 |
| 2001/0016767 A1 | 8/2001 | Wilson et al. | 623/1.11 |
| 2001/0016768 A1 | 8/2001 | Wilson et al. | 623/1.11 |
| 2001/0025195 A1 | 9/2001 | Shaolian et al. | 623/1.13 |
| 2001/0027291 A1 | 10/2001 | Shanley | 604/104 |
| 2001/0027338 A1 | 10/2001 | Greenberg | 623/1.13 |
| 2001/0029396 A1 | 10/2001 | Wilson et al. | 623/1.11 |
| 2001/0037116 A1 | 11/2001 | Wilson et al. | 606/108 |
| 2001/0037138 A1 | 11/2001 | Wilson et al. | 623/1.11 |
| 2001/0039448 A1 | 11/2001 | Dibie | 623/1.16 |
| 2001/0049552 A1 | 12/2001 | Richter et al. | 623/1.15 |
| 2001/0056297 A1 | 12/2001 | Hojeibane | 623/1.16 |
| 2002/0013618 A1 | 1/2002 | Marotta et al. | 623/1.15 |
| 2002/0013619 A1 | 1/2002 | Shanley | 623/1.15 |
| 2002/0022874 A1 | 2/2002 | Wilson | 623/1.11 |
| 2002/0026232 A1 | 2/2002 | Marotta et al. | 623/1.16 |
| 2002/0035392 A1 | 3/2002 | Wilson | 623/1.11 |
| 2002/0042650 A1 | 4/2002 | Vardi et al. | 623/1.35 |
| 2002/0052648 A1 | 5/2002 | McGuckin, Jr. et al. | 623/1.35 |
| 2002/0055770 A1 * | 5/2002 | Doran et al. | 623/1.15 |
| 2002/0072790 A1 | 6/2002 | McGuckin, Jr. et al. | 623/1.12 |
| 2002/0111675 A1 | 8/2002 | Wilson | 623/1.35 |
| 2002/0156516 A1 | 10/2002 | Vardi et al. | 623/1.11 |

| | | | | | | |
|---|---|---|---|---|---|---|
| 2002/0156517 A1 | 10/2002 | Perouse | 623/1.11 | EP | 0895759 | 2/1999 |
| 2002/0165604 A1 | 11/2002 | Shanley | 623/1.15 | EP | 0904745 | 3/1999 |
| 2002/0173835 A1 | 11/2002 | Bourang et al. | 623/1.11 | EP | 0937442 | 8/1999 |
| 2002/0173840 A1 | 11/2002 | Brucker et al. | 623/1.16 | EP | 0347023 | 12/1999 |
| 2002/0183763 A1 | 12/2002 | Callol et al. | 606/108 | EP | 1031328 | 8/2000 |
| 2002/0193872 A1 | 12/2002 | Trout, III et al. | 623/1.34 | EP | 1031329 | 8/2000 |
| 2002/0193873 A1 | 12/2002 | Brucker | 623/1.11 | EP | 0883384 | 12/2000 |
| 2003/0009209 A1 | 1/2003 | Hojeibane | 623/1.11 | EP | 0862392 | 8/2001 |
| 2003/0028233 A1 | 2/2003 | Vardi et al. | 623/1.11 | EP | 0808140 | 12/2001 |
| 2003/0050688 A1 | 3/2003 | Fischell et al. | 623/1.15 | EP | 0884028 | 2/2002 |
| 2003/0055378 A1 | 3/2003 | Wang et al. | 604/103.07 | EP | 1190685 | 3/2002 |
| 2003/0055483 A1 | 3/2003 | Gumm | 623/1.11 | EP | 0897700 | 7/2002 |
| 2003/0074047 A1 | 4/2003 | Richter | 623/1.11 | EP | 0684022 | 2/2004 |
| 2003/0093109 A1 | 5/2003 | Mauch | 606/194 | EP | 1157674 | 7/2005 |
| 2003/0097169 A1 | 5/2003 | Brucker | 623/1.11 | EP | 1031330 | 11/2005 |
| 2003/0114912 A1 | 6/2003 | Sequin et al. | 623/1.11 | EP | 1070513 | 6/2006 |
| 2003/0125791 A1 | 7/2003 | Sequin et al. | 623/1.11 | FR | 2678508 | 1/1993 |
| 2003/0125802 A1 | 7/2003 | Callol et al. | 623/1.35 | FR | 2740346 | 10/1995 |
| 2003/0135259 A1 | 7/2003 | Simso | 623/1.12 | FR | 2756173 | 11/1996 |
| 2003/0181923 A1 | 9/2003 | Vardi | 606/108 | GB | 2337002 | 5/1998 |
| 2003/0195606 A1 | 10/2003 | Davidson et al. | 623/1.11 | WO | 88/06026 | 8/1988 |
| 2004/0006381 A1 | 1/2004 | Sequin et al. | 623/1.12 | WO | 95/21592 | 8/1995 |
| 2004/0015227 A1 | 1/2004 | Vardi et al. | 623/1.16 | WO | 96/29955 | 10/1996 |
| 2004/0044396 A1 | 3/2004 | Clerc et al. | 623/1.13 | WO | 96/34580 | 11/1996 |
| 2004/0059406 A1 | 3/2004 | Cully et al. | 623/1.11 | WO | 96/41592 | 12/1996 |
| 2004/0088007 A1 | 5/2004 | Eidenschink | 607/1 | WO | 97/07752 | 3/1997 |
| 2004/0117003 A1 | 6/2004 | Ouriel et al. | 623/1.35 | WO | 97/15346 | 5/1997 |
| 2004/0133268 A1 | 7/2004 | Davidson et al. | 623/1.35 | WO | 97/16217 | 5/1997 |
| 2004/0138732 A1 | 7/2004 | Suhr et al. | 623/1.11 | WO | 97/26936 | 7/1997 |
| 2004/0138737 A1 | 7/2004 | Davidson et al. | 623/1.35 | WO | 97/41803 | 11/1997 |
| 2004/0148006 A1 | 7/2004 | Davidson et al. | 623/1.11 | WO | 97/45073 | 12/1997 |
| 2004/0172121 A1 | 9/2004 | Eidenschink et al. | 623/1.11 | WO | 97/46174 | 12/1997 |
| 2004/0186560 A1 | 9/2004 | Alt | 623/1.35 | WO | 98/19628 | 5/1998 |
| 2004/0225345 A1 | 11/2004 | Fischell et al. | 623/1.11 | WO | 98/36709 | 8/1998 |
| 2004/0267352 A1 | 12/2004 | Davidson | 623/1.11 | WO | 98/37833 | 9/1998 |
| 2005/0004656 A1 | 1/2005 | Das | 623/1.16 | WO | 98/47447 | 10/1998 |
| 2005/0010278 A1 | 1/2005 | Vardi et al. | 623/1.11 | WO | 98/48879 | 11/1998 |
| 2005/0015108 A1 | 1/2005 | Williams et al. | 606/194 | WO | 99/03426 | 1/1999 |
| 2005/0015135 A1 | 1/2005 | Shanley | 623/1.11 | WO | 99/04726 | 2/1999 |
| 2005/0060027 A1 | 3/2005 | Khenansho | | WO | 99/15103 | 4/1999 |
| 2005/0096726 A1 | 5/2005 | Sequin et al. | 623/1.12 | WO | 99/15109 | 4/1999 |
| 2005/0102021 A1 | 5/2005 | Osborne | 623/1.13 | WO | 99/24104 | 5/1999 |
| 2005/0102023 A1 | 5/2005 | Yadin | 623/1.16 | WO | 99/34749 | 7/1999 |
| 2005/0119731 A1 | 6/2005 | Brucker et al. | 623/1.35 | WO | 99/36002 | 7/1999 |
| 2005/0125076 A1 | 6/2005 | Ginn | 623/23.65 | WO | 99/36015 | 7/1999 |
| 2005/0131526 A1 | 6/2005 | Wong | | WO | 99/44539 | 9/1999 |
| 2005/0149161 A1 | 7/2005 | Eidenschink et al. | 623/1.11 | WO | 99/56661 | 11/1999 |
| 2005/0154442 A1 | 7/2005 | Eidenschink et al. | 623/1.11 | WO | 99/65419 | 12/1999 |
| 2005/0154444 A1 | 7/2005 | Quadri et al. | 623/1.23 | WO | 00/07523 | 2/2000 |
| 2005/0182480 A1* | 8/2005 | Doran et al. | 623/1.15 | WO | 00/10489 | 3/2000 |
| 2005/0183259 A1 | 8/2005 | Eidenschink et al. | 29/508 | WO | 00/16719 | 3/2000 |
| 2005/0209673 A1 | 9/2005 | Shaked | 623/1.11 | WO | 00/27307 | 5/2000 |
| 2005/0228483 A1 | 10/2005 | Kaplan | 623/1.11 | WO | 00/27463 | 5/2000 |
| 2006/0036315 A1 | 2/2006 | Yadin et al. | 623/1.35 | WO | 00/28922 | 5/2000 |
| 2006/0041303 A1 | 2/2006 | Israel | 623/1.11 | WO | 00/44307 | 8/2000 |
| 2006/0079956 A1 | 4/2006 | Eigler et al. | 623/1.35 | WO | 00/44309 | 8/2000 |
| 2006/0173528 A1 | 8/2006 | Feld et al. | 623/1.15 | WO | 00/47134 | 8/2000 |
| 2007/0005126 A1 | 1/2007 | Tischler | | WO | 00/48531 | 8/2000 |
| 2007/0073376 A1 | 3/2007 | Krolik et al. | 623/1.11 | WO | 00/49951 | 8/2000 |
| | | | | WO | 00/51523 | 9/2000 |
| | FOREIGN PATENT DOCUMENTS | | | WO | 00/57813 | 10/2000 |
| | | | | WO | 00/67673 | 11/2000 |
| DE | 9014845 | 2/1991 | | WO | 00/71054 | 11/2000 |
| DE | 29701758 | 3/1997 | | WO | 00/71055 | 11/2000 |
| DE | 29701883 | 5/1997 | | WO | 00/74595 | 12/2000 |
| EP | 0479730 | 10/1991 | | WO | 01/21095 | 3/2001 |
| EP | 0751752 | 1/1997 | | WO | 01/21109 | 3/2001 |
| EP | 0783873 | 7/1997 | | WO | 01/21244 | 3/2001 |
| EP | 0804907 | 11/1997 | | WO | 01/35715 | 5/2001 |
| EP | 0479557 | 7/1998 | | WO | 01/35863 | 5/2001 |
| EP | 0876805 | 11/1998 | | WO | 01/39697 | 6/2001 |
| EP | 0880949 | 12/1998 | | WO | 01/39699 | 6/2001 |
| EP | 0891751 | 1/1999 | | WO | 01/41677 | 6/2001 |

| | | |
|---|---|---|
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 01/70299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2006/028925 | 3/2006 |

OTHER PUBLICATIONS

U.S. Appl. No. 09/614,472, filed Jul. 11, 2000, Davidson et al.
U.S. Appl. No. 09/663,111, filed Sep. 15, 2000, Davidson et al.
Chevalier, M.D., Bernard, "Placement of Coronary Stents in Bifurcation Lesions by the "Culotte" Technique," *The American Journal of Cardiology*, vol. 82, pp. 943-949 (Oct. 15, 1998).
Nakamura M.D., Shigeru, "Techniques for Palmaz-Schatz Stent Deployment in Lesions with a Large Side Branch," *Catheterization and Cardiovascular Diagnosis*, vol. 34, pp. 353-361 (1995).
Caputo, Ronald P., "Stent Jail: A Minimum-Security Prison," *The American Journal of Cardiology*, vol. 77, pp. 1226-1230 (Jun. 1, 1996).
Colombo, M.D., Antonio, ""Kissing" Stent for Bifurcational Coronary Lesion," *Catheterization and Cardiovascular Diagnosis*, vol. 30, pp. 327-330 (Dec. 1993).
Carrie, M.D., Didier, ""T"-Shaped Stent Placement: A Technique for the Treatment of Dissected Bifurcation Lesions," *Catheterization and Cardiovascular Diagnosis*, vol. 37, pp. 311-313 (Mar. 1996).
Katoh, M.D., Osamu, "New Double Wire Technique to Stent Ostial Lesions," *Catheterization and Cardiovascular Diagnosis*, vol. 40, pp. 400-402 (Apr. 1997).
Lewis, M.D., Bruce E., "Acute procedural results in the treatment of 30 coronary artery bifurcation lesions with a double-wire atherectomy technique for side-branch protection," *American Heart Journal*, vol. 127:6, pp. 1600-1607 (Jun. 1994).
Yamashita; M.D.,PhD., Takehiro, "Bifurcation Lesions: Two Stents Versus One Stent—Immediate and Follow-up Results," *Journal of the American College of Cardiology*, vol. 35:5, pp. 1145-1151 (Apr. 2000).
Satler, M.D., Lowell F., "Bifurcation Disease: To Treat of Not to Treat," *Catheterization and Cardiovascular Interventions*, vol. 50, pp. 411-412 (2000).

* cited by examiner

BIFURCATION STENT PATTERN

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Stents may be arranged for bifurcations and may include outwardly deployable side branch structure. However, because expansion characteristics of the side branch structure are often different than portions of the stent, stent designs that would be sufficiently flexible to traverse a tortuous anatomy in an unexpanded state sometimes would not provide adequate vessel support in the expanded state.

There remains a need for stent patterns that provide proper scaffolding support and drug delivery in the expanded state, while also allowing for crimpability and for flexibility and deliverability in the unexpanded state.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a stent having a proximal end and a distal end. The stent further comprises a plurality of interconnected strut members defining a plurality of cells. A portion of the interconnected strut members comprise a side branch structure defining a side branch cell, wherein the side branch cell is shaped differently than other cells of the stent. The interconnected strut members further define a plurality of serpentine bands and a plurality of connector struts. Adjacent serpentine bands are connected by at least one connector strut. A first serpentine band has a first band axis, and at least a portion of the first band axis extends circumferentially about a portion of the stent. A second serpentine band has a second band axis, and at least a portion of the second band axis extends helically about a portion of the stent.

In at least one other embodiment, a stent may be made according to a flat pattern comprising a plurality of interconnected strut members defining a plurality of cells. A portion of the interconnected strut members comprise a side branch structure defining a side branch cell, the side branch cell being shaped differently than other cells of the stent. The interconnected strut members further define a plurality of serpentine bands and a plurality of connector struts. Adjacent serpentine bands are connected by at least one connector strut. A first serpentine band has a first band axis, and at least a portion of the first band axis extends perpendicular to a stent lengthwise axis. A second serpentine band has a second band axis, and at least a portion of the second band axis extends at a non-perpendicular angle to the stent lengthwise axis.

In at least one other embodiment, a stent comprises a plurality of interconnected strut members defining a plurality of cells. A portion of the interconnected strut members comprise a side branch structure defining a side branch cell, the side branch cell being shaped differently than other cells of the stent. The interconnected strut members further define a plurality of serpentine bands and a plurality of connector struts. Adjacent serpentine bands are connected by at least one connector strut. Each serpentine band comprises a plurality of proximal peaks and distal valleys. A first serpentine band is connected to the side branch structure and a second serpentine band is connected to the side branch structure. A third serpentine band and a fourth serpentine band are not directly connected to the side branch structure. A first connector strut is connected at one end to a distal valley of the first serpentine band and connected at a second end to a proximal peak of the second serpentine band. A second connector strut is connected at one end to a distal valley of the third serpentine band and connected at a second end to a distal valley of the fourth serpentine band.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
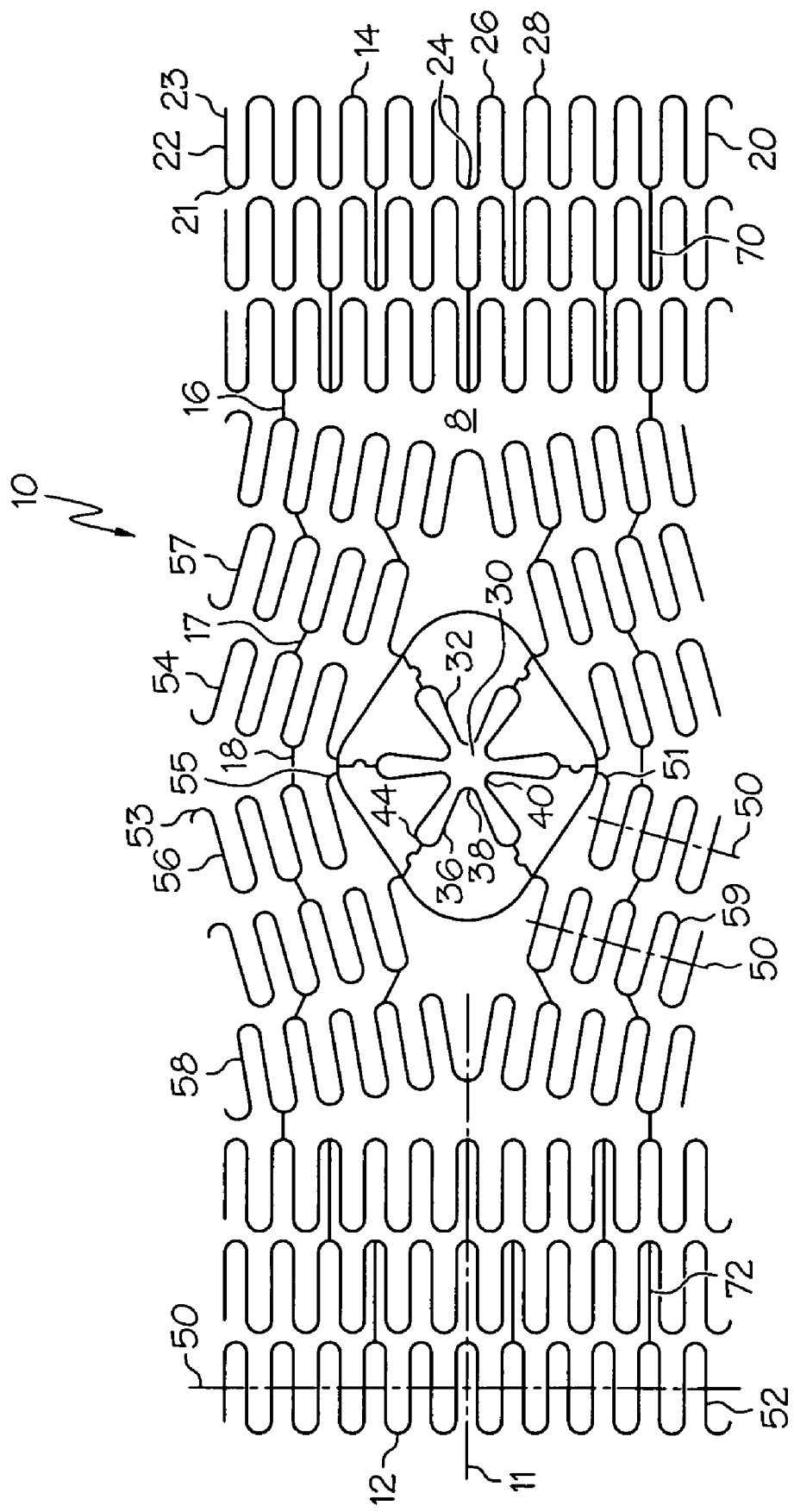
FIG. 1 shows a flat pattern for an embodiment of a stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of a flat pattern for a stent 10. The stent 10 may have a proximal end 12 and a distal end 14, and may comprise a plurality of serpentine bands 20. Each serpentine band 20 may comprise a plurality of struts 22, each strut 22 having a first end 21 and a second end 23. Circumferentially adjacent struts 22 within a serpentine band 20 may be connected by turns 28. Turns 28 located on a proximal side of a serpentine band 20 may comprise proximal peaks 24, and turns 28 located on a distal side of a serpentine band 20 may comprise distal valleys 26.

Serpentine bands 20 which are adjacent to one another along the length of the stent 10 may be connected by at least one connector strut 16. A connector strut 16 may span between turns 28 of adjacent serpentine bands 20. For example, a first end of a connector strut 16 may connect to a distal valley 26 of one serpentine band 20, and a second end of the connector strut 16 may connect to a proximal peak 24 of an adjacent serpentine band 20. In some embodiments, a connector strut 16 may connect to any portion of a serpentine band 20, such as a strut 22. A connector strut 16 may have any suitable shape and may be straight along its length, or in some embodiments may have curvature, bends, inflection points, etc.

The interconnected stent elements, such as struts 22, turns 28 and connector struts 16, may define a stent wall portion and may further define a plurality of cells 8. Each cell 8 may comprise an aperture or void in the stent wall portion.

The stent 10 may further comprise a side branch cell or opening 30, which may comprise a cell 8 that is different than other cells 8 of the stent 10. For example, a side branch cell 30 may be shaped differently, may have a larger or smaller area, and/or may extend about the circumference or along the length of the stent 10 to a greater or lesser extent than any other cell 8 included in the stent 10.

The side branch cell 30 desirably includes side branch structural elements 32. In some embodiments, the side branch structure 32 may define a plurality of side branch petals 40 which may have any suitable size and shape, and may each be oriented in any suitable direction. Petals 40 may be arranged to deploy outwardly when the stent 10 is expanded. Each petal 40 may comprise a plurality of struts 36 and at least one turn 38. A strut 36 may be straight along its length, and may be oriented in any suitable direction. A turn 38 may be oriented in any suitable direction and in some embodiments may be oriented toward the center of the side branch cell 30. Petals 40 which are adjacent to one another about the side branch cell 30 may be connected to one another by a connecting portion 44.

Various serpentine bands 20 may have various orientations within the stent 10. Each serpentine band 20 may generally have an approximate longitudinal axis 50. In some embodiments, the longitudinal axis 50 of a given serpentine band 20 may bisect or intersect the midpoint of each strut 22 included in the serpentine band 20. The longitudinal axis 50 of a serpentine band 20 may extend the entire length of the serpentine band 20.

When the stent 10 is viewed as a flat pattern, the longitudinal axes 50 of various serpentine bands 20 may be oriented at various angles to a stent lengthwise axis 11. For example, a serpentine band 52 may be located at the proximal end 12 of the stent 10 and may have an axis 50 that is perpendicular to the stent lengthwise axis 11. Some serpentine bands 56, 59 may be connected to the side branch structure 32 and may have an axis 50, and at least a portion of the axis 50 may be non-perpendicular to the stent lengthwise axis 11 or may be oriented at an oblique angle to the stent lengthwise axis 11. In some embodiments, serpentine bands 20 located toward the proximal or distal ends of the side branch cell 30 may be canted to a higher degree than serpentine bands 20 located toward the center of length of the side branch cell 30.

In some embodiments, some serpentine bands 58 that are not directly connected to the side branch structure 32 may have an axis 50, and at least a portion of the axis 50 may be non-perpendicular to the stent lengthwise axis 11 or may be oriented at an oblique angle to the stent lengthwise axis 11.

In some embodiments, at least a portion of a serpentine band 20 may have an axis 50 that is non-perpendicular to the stent lengthwise axis 11. Any suitable portion of length of the serpentine band may have such an orientation. For example, in various embodiments, at least ¼, at least ⅓, or at least ½ of the length of the band 20 may have an axis 50 that is non-perpendicular to the stent lengthwise axis 11.

In some embodiments, serpentine bands 20 may flare outwardly from the side branch structure 32. For example, a serpentine band 56 may have a first end 51 and a second end 55, each end contacting an element of the side branch structure 32. The serpentine band 56 may further have a midpoint 53 located along the serpentine band 56 opposite the side branch structure 32. A serpentine band 20 which is considered to flare outwardly may have a midpoint 53 that is located closer to the closest end 12 of the stent 10 than either end 51, 55 of the serpentine band 20.

In some embodiments, serpentine bands 20 located to the proximal side of the side branch cell 30 may flare toward the proximal end 12 of the stent 10. Serpentine bands 20 located to the distal side of the side branch cell 30 may flare toward the distal end 14 of the stent 10. In some embodiments, serpentine bands 20 may flare outwardly to a greater degree as the stent 10 is traversed from the middle of the side branch cell 30 outwardly towards either end of the side branch cell 30. The amount of flaring may then reduce as the stent 10 is traversed from the end of the side branch cell 30 to the associated end 12 or 14 of the stent 10.

In some embodiments, the side branch structure 32 may define a generally circular or oval shaped area. A serpentine band 20 which is considered to flare outwardly may have an axis 50 oriented in a radial direction of the side branch structure shape.

In some embodiments, when the stent 10 is in a cylindrical configuration, at least a portion of an axis 50 of a serpentine band 20 may be oriented in a stent circumferential direction. A circumference of the stent 10 may be oriented orthogonally to the stent lengthwise axis 11. Serpentine bands 20 having a generally circumferentially oriented axis 50 may be located anywhere on the stent 10, such as near an end 12, 14 of the stent 10, or anywhere along the length of the stent 10. In some embodiments, a serpentine band 54 having a circumferentially oriented axis 50 may be connected to an element of the side branch structure 32.

In some embodiments, when the stent 10 is in a cylindrical configuration, at least a portion of an axis 50 of a serpentine band 20 may spiral or may extend generally helically about a portion of the stent 10. An axis 50 that is oriented at an angle to the stent lengthwise axis 11 when the stent 10 is viewed as a flat pattern may be oriented helically when the stent 10 has a cylindrical configuration. Any suitable portion of length of the serpentine band 20 may have such an orientation. For example, in various embodiments, at least ¼, at least ⅓, or at least ½ of the length of the band 20 may have an axis 50 that is non-perpendicular to the stent lengthwise axis 11. In some embodiments, a serpentine band 20 may have a first portion of length, such as a first half of length, having an axis 50 oriented in a first spiral or generally helical orientation, and may have a second portion of length, such as a second half of length, having an axis 50 oriented in a second spiral or generally helical orientation. In some embodiments, the first generally helical orientation may comprise a mirror image of the second generally helical orientation.

In some embodiments, connector struts 16 which span between serpentine bands 20 located near the side branch cell 30 may extend between turns 28 that are close to one another. For example, a connector strut 17 may be connected at one end to a distal valley 26 of a serpentine band 54 and may be connected at the other end to a proximal peak 24 of an adjacent band 57. Another connector strut 18 may be connected at one end to a proximal peak 24 of the serpentine band 54 and may be connected at the other end to a distal valley 26 of another adjacent serpentine band 56. In some embodiments, a single strut 22 of the serpentine band 54 may be located between the turns 28 to which the connector struts 17, 18 are connected. In some embodiments, each of the serpentine bands 54, 56, 57 may be connected to elements of the side branch structure 32. In some embodiments, a plurality of turns 28 which are not connected to a connector strut 16 may be oriented between the side branch structure 32 and a connector strut 16. For example, four, five, six or seven turns 28 may be oriented between the side branch structure 32 and a connector strut 16.

Connector struts 16 which span between close turns 28, such as adjacent proximal peaks 24 and distal valleys 28, may cause the axes 50 of the adjacent serpentine bands 20 to move toward one another in the region of the connector strut 16 as the stent 10 is expanded. Therefore, in some embodiments, the connector struts 16 may be positioned to cause reorientation of serpentine bands 20 during expansion. In some embodiments, a plurality of serpentine bands 54, 56, 57, 59 may each connect to elements of side branch structure at either end 51, 55, and connector struts 16 may span between close turns 28 of the bands 54, 56, 57, 59. In an unexpanded state, some or all of the bands 54, 56, 57, 59 may flare outwardly, having an axis 50 that is non-perpendicular to the stent lengthwise axis 11. As the stent 10 is expanded, the axes 50 of the bands 54, 56, 57, 59 may move toward one another in the region of the connector struts 16, thereby reorienting the serpentine bands 54, 56, 57, 59.

Figure 2:
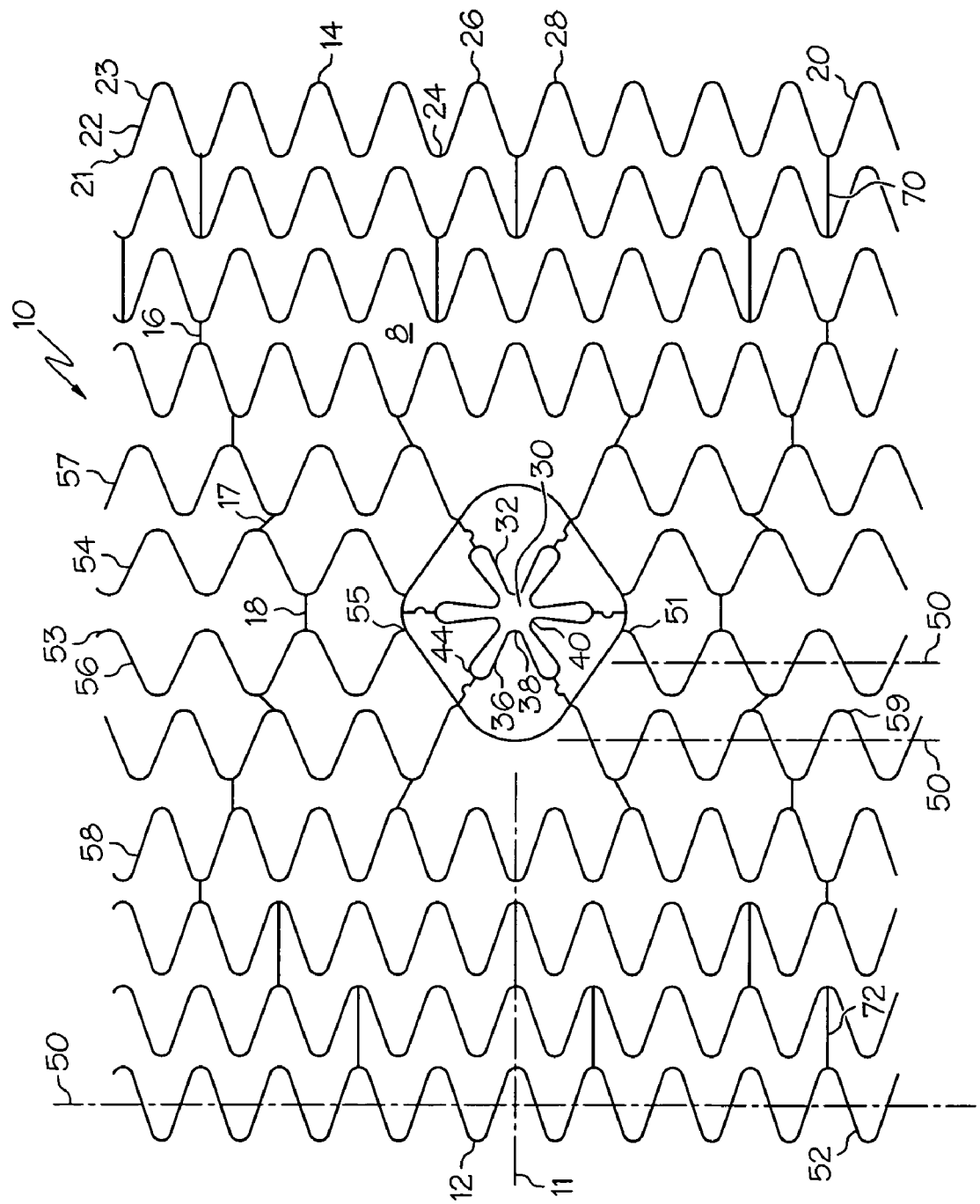
FIG. 2 shows a flat pattern for the stent of FIG. 1 in an expanded state.

FIG. 2 shows the stent pattern of FIG. 1 in an expanded state. The axes 50 of various serpentine bands 20 may be parallel to one another. For example, the axes 50 of serpentine bands 54, 56, 57, 59 are parallel to one another.

In some embodiments, serpentine bands 20 which flare outwardly in the unexpanded state may reorient during expansion and have axes 50 which are oriented in a stent circumferential direction when the stent 10 is expanded. Therefore, in some embodiments, the connector struts 16 may be arranged to pull more structural stent elements into regions adjacent to the side branch cell 30 during stent expansion. This allows for proper drug delivery and scaffolding support in the expanded state while also providing for greater crimpability and greater flexibility and deliverability in the unexpanded state.

In some embodiments, connector struts 16 may span between similar portions of adjacent serpentine bands 20. For example, connector strut 70 may span from a proximal peak 24 of one serpentine band 20 to a proximal peak 24 of an adjacent serpentine band 20. Connector strut 72 may span from a distal valley 26 of one serpentine band 20 to a distal valley 26 of an adjacent serpentine band 20. Connector struts 16 which connect serpentine bands 20 that are located proximal or distal to the side branch cell 30 may span between similar portions of the serpentine bands 20. This type of connector strut 16 configuration may lead to the axes 50 of the serpentine bands 20 maintaining the same spacing during and after stent expansion.

Figure 3:
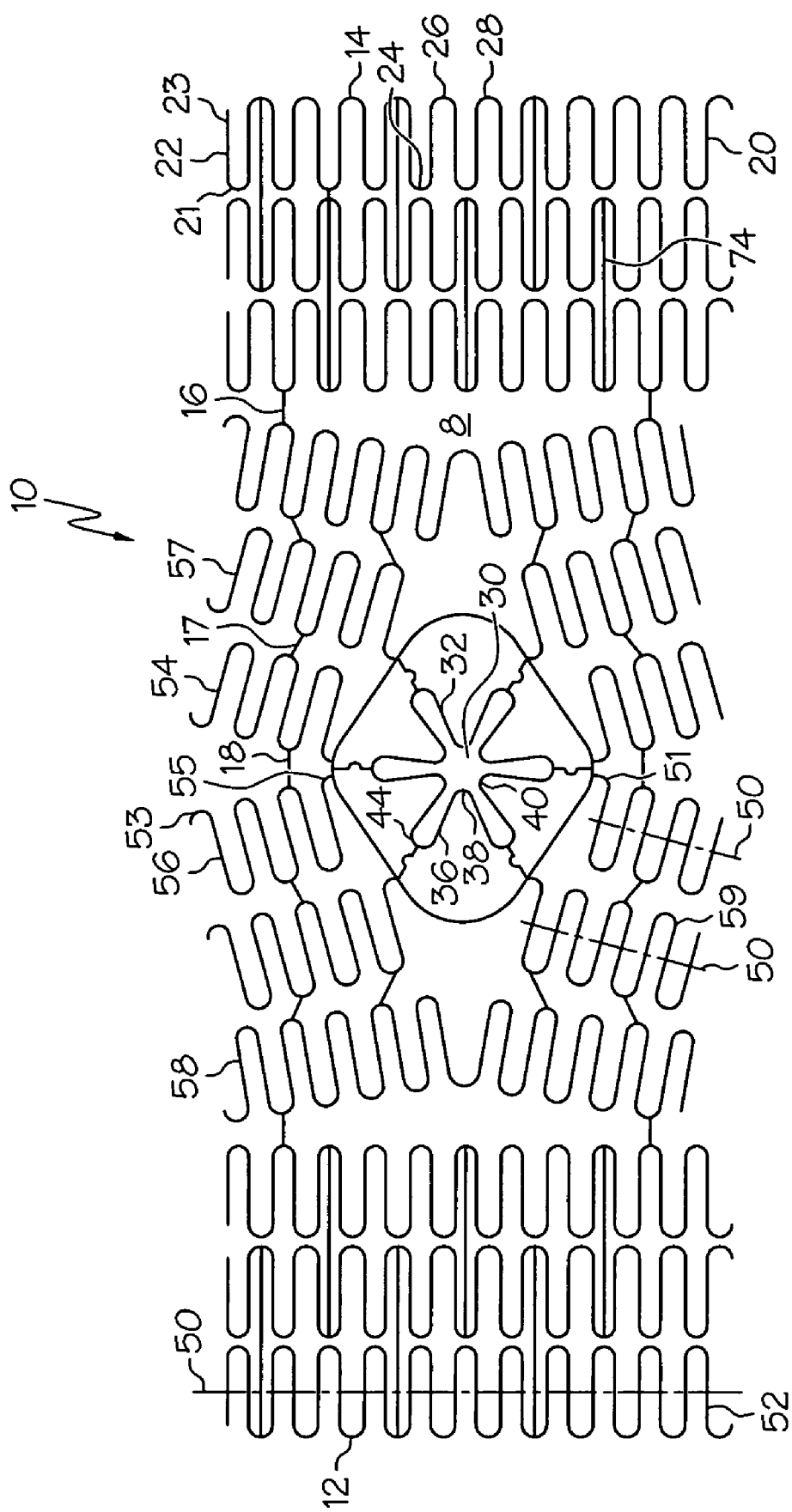
FIG. 3 shows a flat pattern for another embodiment of a stent.
Figure 4:
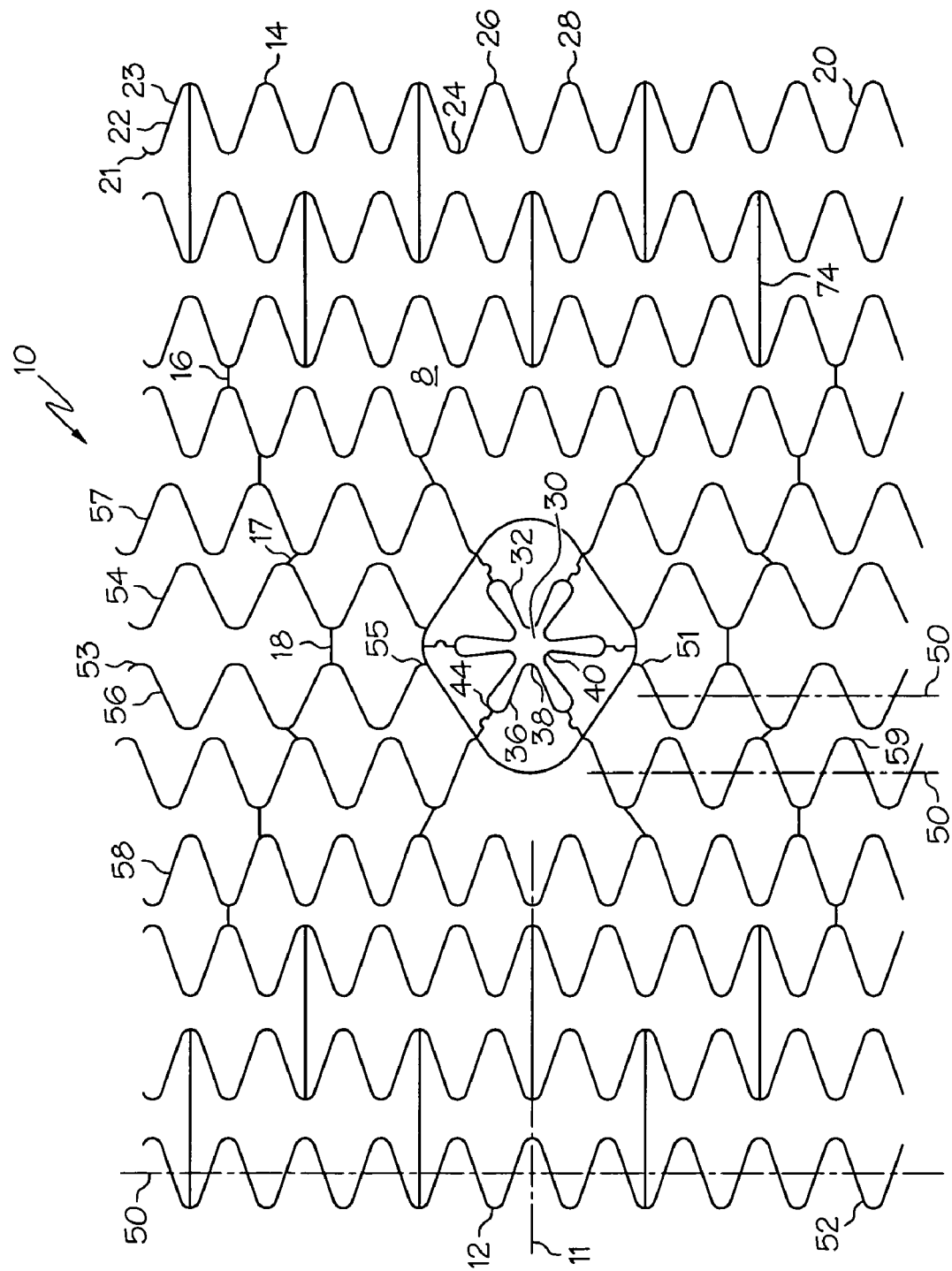
FIG. 4 shows a flat pattern for the stent of FIG. 3 in an expanded state.

Referring to FIGS. 3 and 4, in some embodiments, connector struts 16 may span between opposing or far turns 28 of adjacent serpentine bands. For example, connector strut 74 may span from a proximal peak 24 of one serpentine band 20 to a distal valley 26 of an adjacent serpentine band 20. This type of connector strut 16 configuration may lead to the axes 50 of the serpentine bands 20 moving away from one another in the region of the connector strut 16 during stent expansion.

The location of connector struts 16 and locations of connections to the serpentine bands 20 may be selected to provide a stent 10 in which a portion of the serpentine bands 20 move toward one another in some areas of the stent 10 and a portion of the serpentine bands 20 move away from one another in other areas of the stent 10. For example, a stent 10 may be arranged to pull more structural stent elements into regions adjacent to the side branch cell 30 during stent expansion while at the same time exhibiting minimal foreshortening along its length.

In some embodiments, connector struts 16 which connect to a serpentine band 20 which connects directly to a side branch element 32 may extend between close turns 28 of the serpentine bands 20. In some embodiments, connector struts 16 which connect between serpentine bands 20 that are located proximal or distal to the side branch cell 30 may extend between far turns 28 of the serpentine bands.

In some embodiments, a serpentine band 20 may have a length as measured along the axis 50 of the band 20. Serpentine bands 20 which connect to side branch structure 32 may be measured from a first end 51 to a second end 55. In some embodiments, the length of a serpentine band 20 may be equal to a circumference of the stent 10. For example, serpentine band 52 may have a length equal to a circumference of the stent 10. This may be true in both an unexpanded state and an expanded state.

In some embodiments, the length of a serpentine band 20 may be greater than a circumferential component as measured from a first end 51 to a second end 55 of the band 20 about the circumference of the stent 10. Serpentine bands 20 having an axis 50 that is oriented generally helically about the stent 10 may have a length that is greater than a circumferential component of the stent 10 as measured from a first end 51 to a second end 55 of the band 20. In some embodiments, this may be true in both unexpanded and expanded states. In some embodiments, for example wherein the axes 50 of adjacent serpentine bands 20 move toward one another during stent expansion, the length of a serpentine band 20 may be greater than a circumferential component as measured from a first end 51 to a second end 55 of the band 20 when the stent 10 is unexpanded, and the length of the serpentine band 20 may be equal to a circumferential component as measured from a first end 51 to a second end 55 of the band 20 when the stent 10 is expanded.

The invention is further directed to methods of manufacturing a stent 10 according to the designs disclosed herein. The invention is further directed to methods of delivering and expanding a stent 10 as described herein.

Some embodiments of delivery catheters which may be suitable for delivering and deploying stents as described herein are disclosed in U.S. Pat. No. 6,835,203 and US Published Application No. 20050060027, the entire disclosures of which are hereby incorporated herein in their entireties.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent having a proximal end and a distal end, the stent comprising:

a plurality of interconnected strut members defining a plurality of cells, a portion of the interconnected strut members comprising a side branch structure defining a side branch cell, the side branch cell being shaped differently than other cells of the stent;

the interconnected strut members further defining a plurality of serpentine bands and a plurality of connector struts, adjacent serpentine bands connected by at least one connector strut;

a first serpentine band having a first band axis, at least a portion of the first band axis extending generally circumferentially about a portion of the stent;

a second serpentine band having a second band axis, at least ¼ of the length of the second band axis extending generally helically about a portion of the stent; and a third serpentine band having a third band axis, the third serpentine band adjacent to the second serpentine band, the third band axis extending parallel to the second band axis.

2. The stent of claim 1, wherein the first serpentine band is located at an end of the stent.

3. The stent of claim 1, wherein the second serpentine band is connected to the side branch structure.

4. The stent of claim 3, further comprising a connector strut connecting at one end to a distal valley of the second serpentine band and at another end to a proximal peak of the third serpentine band.

5. The stent of claim 4, wherein the third serpentine band is connected to the side branch structure.

6. The stent of claim 4, further comprising a fourth serpentine band, the fourth serpentine band adjacent to the second serpentine band; a connector strut connecting at one end to a distal valley of the fourth serpentine band and at another end to a proximal peak of the second serpentine band.

7. The stent of claim 3, wherein the second serpentine band comprises a plurality of struts connected by turns, and at least four turns are located between the side branch structure and a connector strut connected to the second serpentine band.

8. The stent of claim 1 in an unexpanded state.

9. The stent of claim 8, wherein after expansion of the stent, at least a portion of the second band axis extends circumferentially about a portion of the stent.

10. The stent of claim 1, wherein after expansion of the stent, the first band axis is parallel to the second band axis.

11. The stent of claim 1, wherein said second serpentine band comprises a plurality of struts, each strut being straight along its length.

12. The stent of claim 11, wherein each straight strut of said second serpentine band has the same length.

13. A stent having a proximal end and a distal end, the stent comprising:

a plurality of interconnected strut members defining a plurality of cells, a portion of the interconnected strut members comprising a side branch structure defining a side branch cell, the side branch cell being shaped differently than other cells of the stent;

the interconnected strut members further defining a plurality of serpentine bands and a plurality of connector struts, adjacent serpentine bands connected by at least one connector strut;

a first serpentine band having a first band axis, at least a portion of the first band axis extending generally circumferentially about a portion of the stent;

a second serpentine band having a second band axis, at least ¼ of the length of the second band axis extending generally helically about a portion of the stent, the second serpentine band connected to the side branch structure;

a third serpentine band adjacent to the second serpentine band, a connector strut connecting at one end to a distal valley of the second serpentine band and at another end to a proximal peak of the third serpentine band; and a fourth serpentine band adjacent to the second serpentine band, a connector strut connecting at one end to a distal valley of the fourth serpentine band and at another end to a proximal peak of the second serpentine band;

wherein the fourth serpentine band is connected to the side branch structure.

14. A stent, a flat pattern for the stent comprising:

a plurality of interconnected strut members defining a plurality of cells, a portion of the interconnected strut members comprising a side branch structure defining a side branch cell, the side branch cell being shaped differently than other cells of the stent;

the interconnected strut members further defining a plurality of serpentine bands and a plurality of connector struts, adjacent serpentine bands connected by at least one connector strut;

a first serpentine band having a first band axis, at least a portion of the first band axis extending perpendicular to a stent lengthwise axis;

a second serpentine band having a second band axis, at least ¼ of the length of the second band axis extending at a non-perpendicular angle to the stent lengthwise axis; and a third serpentine band having a third band axis, the third serpentine band adjacent to the second serpentine band, the third band axis extending parallel to the second band axis.

15. The stent of claim 14, wherein the second serpentine band is connected to the side branch structure.

16. The stent of claim 15, further comprising a connector strut connecting at one end to a distal valley of the second serpentine band and at another end to a proximal peak of the third serpentine band.

17. The stent of claim 16, further comprising a fourth serpentine band, the fourth serpentine band adjacent to the second serpentine band; a connector strut connecting at one end to a distal valley of the fourth serpentine band and at another end to a proximal peak of the second serpentine band.

18. The stent of claim 14 in an unexpanded state, wherein after expansion of the stent, at least a portion of the second band axis extends circumferentially about a portion of the stent.

19. The stent of claim 14, wherein after expansion of the stent, the first band axis is parallel to the second band axis.

20. A stent comprising:

a plurality of interconnected strut members defining a plurality of cells, a portion of the interconnected strut members comprising a side branch structure defining a side branch cell, the side branch cell being shaped differently than other cells of the stent;

the interconnected strut members further defining a plurality of serpentine bands and a plurality of connector struts, adjacent serpentine bands connected by at least one connector strut, each serpentine band comprising a plurality of proximal peaks and distal valleys;

a first serpentine band connected to the side branch structure, the first serpentine band defining a first serpentine band axis that extends helically about a portion of the stent when the stent is unexpanded;

a second serpentine band connected to the side branch structure;

a third serpentine band defining a third serpentine band axis that extends circumferentially around the stent, at least a portion of the first serpentine band axis oriented non-parallel to the third serpentine band axis when the stent is unexpanded, the third serpentine band not directly connected to the side branch structure;

a fourth serpentine band, the fourth serpentine band not directly connected to the side branch structure;

a first connector strut connected at one end to a distal valley of the first serpentine band and connected at a second end to a proximal peak of the second serpentine band; and a second connector strut connected at one end to a distal valley of the third serpentine band and connected at a second end to a distal valley of the fourth serpentine band;

wherein the second serpentine band defines a second serpentine band axis, at least a portion of the second serpentine band axis extending helically about a portion of the stent when the stent is unexpanded, at least a portion of the second serpentine band axis being nonparallel to the first serpentine band axis.

21. The stent of claim 20, wherein after expansion of the stent, the first serpentine band axis is oriented parallel to the third serpentine band axis.

* * * * *

UNITED STATES PATENT AND TRADEMARK OFFICE
CERTIFICATE OF CORRECTION

| | | |
|---|---|---|
| PATENT NO. | : 7,540,881 B2 | Page 1 of 1 |
| APPLICATION NO. | : 11/315084 | |
| DATED | : June 2, 2009 | |
| INVENTOR(S) | : Meyer et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 218 days Delete the phrase "by 218 days" and insert -- by 380 days --

Signed and Sealed this

Fourth Day of May, 2010

David J. Kappos
*Director of the United States Patent and Trademark Office*